US010513580B2

(12) United States Patent
Takimoto et al.

(10) Patent No.: US 10,513,580 B2
(45) Date of Patent: *Dec. 24, 2019

(54) POLYCARBONATE RESIN COMPOSITION

(71) Applicant: IDEMITSU KOSAN CO., LTD., Tokyo (JP)

(72) Inventors: Masami Takimoto, Sodegaura (JP); Takahiro Torii, Chiba (JP); Mitsugu Nakae, Ichihara (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 69 days.

This patent is subject to a terminal disclaimer.

(21) Appl. No.: 15/512,410

(22) PCT Filed: Oct. 15, 2015

(86) PCT No.: PCT/JP2015/079239
§ 371 (c)(1),
(2) Date: Mar. 17, 2017

(87) PCT Pub. No.: WO2016/060220
PCT Pub. Date: Apr. 21, 2016

(65) Prior Publication Data
US 2017/0275422 A1    Sep. 28, 2017

(30) Foreign Application Priority Data

Oct. 17, 2014    (JP) .................................. 2014-212778

(51) Int. Cl.
| | |
|---|---|
| *C08L 69/00* | (2006.01) |
| *C08G 64/08* | (2006.01) |
| *C08L 71/02* | (2006.01) |
| *C08K 5/524* | (2006.01) |
| *C08K 5/526* | (2006.01) |
| *B29C 45/00* | (2006.01) |
| *G01N 30/02* | (2006.01) |

(52) U.S. Cl.
CPC ............ *C08G 64/083* (2013.01); *C08K 5/524* (2013.01); *C08K 5/526* (2013.01); *C08L 69/00* (2013.01); *C08L 71/02* (2013.01); *B29C 45/0001* (2013.01); *G01N 2030/027* (2013.01)

(58) Field of Classification Search
CPC ...... C08G 64/083; C08K 5/524; C08K 5/526; C08L 69/00; C08L 71/02; B29C 45/0001
USPC ....................................................... 524/121
See application file for complete search history.

(56) References Cited

U.S. PATENT DOCUMENTS

| | | | | |
|---|---|---|---|---|
| 9,670,316 | B2* | 6/2017 | Takimoto | ................. C08K 5/55 |
| 9,732,185 | B2* | 8/2017 | Takimoto | ............... C08G 64/06 |
| 9,783,674 | B2* | 10/2017 | Takimoto | ................ C08L 69/00 |
| 10,221,279 | B2* | 3/2019 | Takimoto | ................ C08L 69/00 |
| 2014/0364546 | A1* | 12/2014 | Okamoto | ................. B29B 9/12 |
| | | | | 524/109 |
| 2017/0298176 | A1* | 10/2017 | Takimoto | ............... C08G 64/06 |
| 2018/0187001 | A1* | 7/2018 | Yamazaki | .............. C08K 5/524 |

FOREIGN PATENT DOCUMENTS

| | | |
|---|---|---|
| JP | 4069364 B2 | 4/2008 |
| JP | 2013-139097 A | 7/2013 |
| JP | 2013-231899 A | 11/2013 |
| JP | 2015-093912 A | 5/2015 |
| JP | 2015-180709 A | 10/2015 |
| JP | 6408760 B2 | 10/2018 |
| TW | 201333109 A | 8/2013 |
| TW | 201529715 A | 8/2015 |
| WO | WO-2011/083635 A1 | 7/2011 |
| WO | WO-2013/088796 A1 | 6/2013 |

OTHER PUBLICATIONS

International Search Report issued in International Patent Application No. PCT/JP2015/079239 dated Jan. 12, 2016.
Notice of Reasons for Refusal in JP Patent Application No. 2016-554124 dated May 14, 2019 (10 pages).
Chinese Office Action dated Apr. 30, 2019 in corresponding application No. 201580054619.
Taiwan Office Action issued in Taiwanese Application No. 20150134092 dated Sep. 10, 2019.

* cited by examiner

*Primary Examiner* — Hannah J Pak
(74) *Attorney, Agent, or Firm* — Foley & Lardner LLP

(57) ABSTRACT

Provided is a polycarbonate resin composition, including, with respect to 100 parts by mass of an aromatic polycarbonate resin (A), 0.005 part by mass to 1 part by mass of a phosphorus-based compound (B) having an aryl group, and 0.005 part by mass to 5 parts by mass of a polyether compound (C) having a specific polyoxyalkylene structure, in which: an amount of a compound having a phenol structure produced by decomposition of the phosphorus-based compound (B) 1,500 hours after standing thereof under conditions of 40° C. and a humidity of 90% is 5 mass % or less with respect to the phosphorus-based compound (B); and when a weight of the phosphorus-based compound (B) is measured with a thermogravimetric-differential thermal analysis machine under a nitrogen atmosphere, a temperature at which the weight becomes smaller than the weight before the measurement by 2% is 340° C. or more.

15 Claims, 1 Drawing Sheet

POLYCARBONATE RESIN COMPOSITION

CROSS-REFERENCE TO RELATED APPLICATIONS

The present application is a U.S. national stage application of International Patent Application No. PCT/JP2015/079239, filed Oct. 15, 2015, which claims the benefit of priority to Japanese Patent Application No. 2014-212778, filed Oct. 17, 2014, the entireties of which are hereby incorporated by reference.

TECHNICAL FIELD

The present invention relates to a polycarbonate resin composition.

BACKGROUND ART

An aromatic polycarbonate is excellent in, for example, transparency, mechanical properties, thermal properties, electrical properties, and weatherability, and has been used in an optical molded article, such as a light-guiding plate, a lens, or an optical fiber, through the utilization of its characteristics. However, the light transmittance of the polycarbonate serving as one of the indicators representing its transparency is lower than that of, for example, a polymethyl methacrylate (PMMA). Therefore, a surface light source body including a light-guiding plate made of the aromatic polycarbonate and a light source has a problem in that its luminance is low. Accordingly, the development of a method of improving a luminance and a light transmittance in the light-guiding plate made of the aromatic polycarbonate has been progressing.

In PTL 1, in order to provide a polycarbonate resin composition for a light-guiding plate that is free from becoming opaque and being reduced in transmittance, and that has a satisfactory transmittance and a satisfactory hue, there is a disclosure of an aromatic polycarbonate resin composition for a light-guiding plate obtained by incorporating, into an aromatic polycarbonate resin, a polyoxyalkylene glycol containing a polyethylene glycol or a polypropylene glycol as a main component, or a fatty acid ester thereof.

However, in the method of PTL 1, the heat resistance of the polyoxyalkylene glycol is low, and hence when the composition is molded at a temperature of more than 320° C. or its molding cycle becomes longer, its yellowing becomes serious to largely reduce its luminance and light transmittance, and the reductions may adversely affect the optical performance of a light-guiding product. Further, when the molding is performed at a temperature of more than 340° C., a silver occurs on the surface of a molded article owing to the decomposition gas of the polyoxyalkylene glycol to preclude the article from functioning as the light-guiding product. Accordingly, a temperature increase for an improvement in flowability of the composition is limited, and hence the composition cannot be molded into a thin-walled and large-area light-guiding plate. Therefore, the method is applicable only to some molding materials for small light-guiding plates to be molded at a low temperature around 280° C., and hence its practical range is narrow and insufficient.

In PTL 2, in order to provide an aromatic polycarbonate resin composition capable of resisting molding at high temperature through the alleviation of the insufficient heat resistance serving as a drawback of the method of PTL 1, there is a disclosure of an aromatic polycarbonate resin composition obtained by blending an aromatic polycarbonate resin with a polyoxytetramethylene-polyoxyethylene glycol. According to the method of PTL 2, the composition can be molded in the temperature region of from 280° C. to 340° C. without yellowing.

Meanwhile, in PTL 3, in order to provide a resin composition excellent in heat stability in high-temperature molding and capable of providing a molded article that is excellent in light transmittance and luminance, and that does not cause discoloration or an internal crack after a moist heat resistance test, there is a disclosure of an aromatic polycarbonate resin composition obtained by incorporating a specific diphosphite compound and a specific alicyclic epoxy compound into an aromatic polycarbonate resin. According to the method of PTL 3, the composition can be molded at a temperature of more than 340° C. without yellowing.

CITATION LIST

Patent Literature

PTL 1: JP 4069364 B2
PTL 2: WO 2011/083635 A1
PTL 3: WO 2013/088796 A1

SUMMARY OF INVENTION

Technical Problem

In recent years, additional thinning of a light-guiding plate has been progressing and hence molding may be performed at a temperature of more than 340° C., in particular, a temperature of more than 360° C. From the foregoing viewpoint, the method of PTL 2 is insufficient and hence an additional improvement thereof has been required.

Meanwhile, in the case of some small light-guiding plates that do not need to be thinned, molding is performed at a low temperature around 280° C. Accordingly, an aromatic polycarbonate resin composition that can be molded in an additionally wide temperature region without yellowing has been required. However, in the method of PTL 3, sufficient performance cannot be expressed in the molding temperature region of less than 300° C., though excellent heat stability in high-temperature molding is obtained.

Therefore, the problem to be solved by the present invention is to provide a polycarbonate resin composition that is not reduced in optical characteristics by its deterioration at the time of its molding even when molded in a wide temperature region.

Solution to Problem

The inventors of the present invention have made extensive investigations, and as a result, have found that a polycarbonate resin composition that is not reduced in optical characteristics by its deterioration at the time of its molding even when molded in a wide temperature region can be obtained by blending an aromatic polycarbonate resin with specific amounts of a specific phosphorus-based compound excellent in heat resistance and hydrolysis resistance, and a polyether compound. The inventors have extensively analyzed the working mechanism of the foregoing to elucidate the mechanism. Thus, the inventors have completed the present invention.

That is, according to embodiments of the present invention, there are provided a polycarbonate resin composition and an optical molded article using the composition to be described below.

<1> A polycarbonate resin composition, comprising, with respect to 100 parts by mass of an aromatic polycarbonate resin (A), 0.005 part by mass to 1 part by mass of a phosphorus-based compound (B) having an aryl group, and 0.005 part by mass to 5 parts by mass of a polyether compound (C) having a polyoxyalkylene structure, wherein:

an amount of a compound having a phenol structure produced by decomposition of the phosphorus-based compound (B) 1,500 hours after standing thereof under conditions of 40° C. and a humidity of 90% is 5 mass % or less with respect to the phosphorus-based compound (B);

when a weight of the phosphorus-based compound (B) is measured with a thermogravimetric-differential thermal analysis (TG-DTA) machine under a nitrogen atmosphere, a temperature at which the weight becomes smaller than the weight before the measurement by 2% is 340° C. or more; and the polyether compound (C) is represented by the following formula (1):

$$R^{C3}O—(R^{C1}O)_m(R^{C2}O)_n—R^{C4} \quad (1)$$

wherein $R^{C1}$ and $R^{C2}$ each represent an alkylene group having 1 or more carbon atoms, and $R^{C1}$ and $R^{C2}$ may be identical to or different from each other, m+n represents 5 or more and less than 300, when m represents 2 or more, $R^{C1}$'s may be identical to or different from each other, and when n represents 2 or more, $R^{C2}$'s may be identical to or different from each other, and $R^{C3}$ and $R^{C4}$ each represent a hydrogen atom, a hydrocarbon group having 1 to 30 carbon atoms, an alkanoyl group having 1 to 30 carbon atoms, an alkenoyl group having 2 to 30 carbon atoms, or a glycidyl group, and $R^{C3}$ and $R^{C4}$ may be identical to or different from each other.

<2> The polycarbonate resin composition according to Item <1>, wherein the aromatic polycarbonate resin (A) comprises a polycarbonate comprising, in a main chain thereof, a repeating unit represented by the following general formula (I):

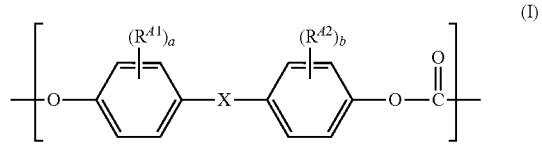

wherein $R^{A1}$ and $R^{A2}$ each independently represent an alkyl group or alkoxy group having 1 to 6 carbon atoms, and $R^{A1}$ and $R^{A2}$ may be identical to or different from each other, X represents a single bond, an alkylene group having 1 to 8 carbon atoms, an alkylidene group having 2 to 8 carbon atoms, a cycloalkylene group having 5 to 15 carbon atoms, a cycloalkylidene group having 5 to 15 carbon atoms, —S—, —SO—, —SO$_2$—, —O—, or —CO—, and a and b each independently represent an integer of from 0 to 4, when a represents 2 or more, $R^{A1}$'s may be identical to or different from each other, and when b represents 2 or more, $R^{A2}$'s may be identical to or different from each other.

<3> The polycarbonate resin composition according to Item <1> or <2>, wherein the phosphorus-based compound (B) comprises a phosphorus-based compound having a phosphite structure.

<4> The polycarbonate resin composition according to any one of Items <1> to <3>, wherein the phosphorus-based compound (B) comprises a pentaerythritol diphosphite compound represented by the following general formula (II):

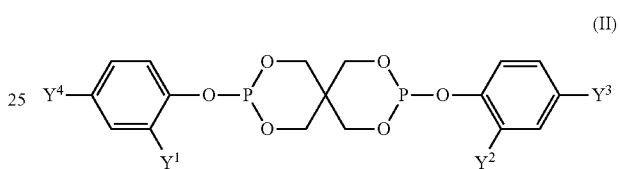

wherein $Y^1$ to $Y^4$ each represent a hydrocarbon group having 6 to 15 carbon atoms, and may be identical to or different from each other.

<5> The polycarbonate resin composition according to Item <4>, wherein $Y^1$ to $Y^4$ in the formula (II) each represent a cumyl group that may be unsubstituted or substituted, a phenyl group that may be unsubstituted or substituted, a naphthyl group that may be unsubstituted or substituted, or a biphenyl group that may be unsubstituted or substituted.

<6> The polycarbonate resin composition according to any one of Items <1> to <5>, wherein the phosphorus-based compound (B) comprises a pentaerythritol diphosphite compound represented by the following general formula (II-1):

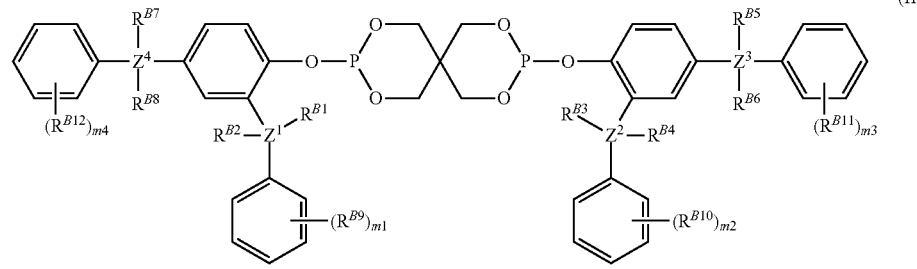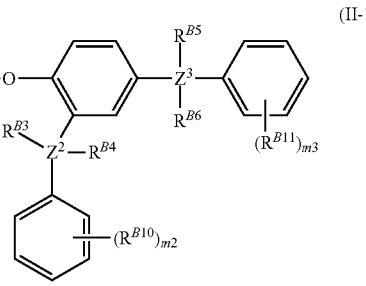

wherein $R^{B1}$ to $R^{B8}$ each represent an alkyl group or an alkenyl group, and may be identical to or different from each other, and $R^{B1}$ and $R^{B2}$, $R^{B3}$ and $R^{B4}$, $R^{B5}$ and $R^{B6}$, or $R^{B7}$ and $R^{B8}$ may be bonded to each other to form a ring, $R^{B9}$ to $R^{B12}$ each represent a hydrogen atom or an alkyl group, and may be identical to or different from each other, m1 to m4 each represent an integer of from 0 to 5, and may be identical to or different from each other, and $Z^1$ to $Z^4$ each represent a single bond or a carbon atom, and may be identical to or different from each other, and when $Z^1$ to $Z^4$ each represent a single bond, $R^{B1}$ to $R^{B8}$ are excluded from the general formula (II-1).

<7> The polycarbonate resin composition according to any one of Items <1> to <6>, wherein the phosphorus-based compound (B) comprises bis(2,4-dicumylphenyl)pentaerythritol diphosphite.

<8> The polycarbonate resin composition according to any one of Items <1> to <7>, wherein the polyether compound (C) comprises a polyoxyalkylene glycol in which in the formula (1), $R^{C1}$ and $R^{C2}$ each represent an alkylene group having 2 to 5 carbon atoms, and $R^{C3}$ and $R^{C4}$ each represent a hydrogen atom.

<9> The polycarbonate resin composition according to any one of Items <1> to <8>, wherein the aromatic polycarbonate resin (A) has a viscosity-average molecular weight (Mv) of from 9,000 to 50,000.

<10> The polycarbonate resin composition according to any one of Items <1> to <9>, wherein an amount of o-hydroxyacetophenone measured by the following measurement method (2) is 2.0 ppm by mass or less, and an amount of o-hydroxyacetophenone measured by the following measurement method (1) is twice or less as large as the amount of o-hydroxyacetophenone measured by the measurement method (2):

Measurement Method (1)

a polycarbonate resin molding material is pelletized, followed by drying, and is then molded into a molded body measuring 50 mm by 80 mm by 5 mm thick by an injection molding method at a cylinder temperature of 360° C. and a die temperature of 80° C. for a cycle time of 50 seconds, the molded body is pulverized and dissolved in chloroform, and an amount of o-hydroxyacetophenone in the solution is determined by high-performance liquid chromatography; and Measurement Method (2)

the polycarbonate resin molding material is pelletized, followed by drying, and is then molded into a molded body measuring 50 mm by 80 mm by 5 mm thick by the injection molding method at a cylinder temperature of 280° C. and a die temperature of 80° C. for a cycle time of 50 seconds, the molded body is pulverized and dissolved in chloroform, and an amount of o-hydroxyacetophenone in the solution is determined by the high-performance liquid chromatography.

<11> The polycarbonate resin composition according to any one of Items <1> to <10>, wherein YI values measured by the following measurement methods (3) and (4) are 1.2 or less, and a difference between the YI values measured by the measurement method (3) and the measurement method (4) is 0.1 or less:

Measurement Method (3)

a polycarbonate resin molding material is pelletized, followed by drying, and is then molded into a molded body measuring 50 mm by 80 mm by 5 mm thick by an injection molding method at a cylinder temperature of 360° C. and a die temperature of 80° C. for a cycle time of 50 seconds, and a YI value of the molded body is measured with a spectrophotometer under conditions of a C light source and a two-degree field of view; and Measurement Method (4)

the polycarbonate resin molding material is pelletized, followed by drying, and is then molded into a molded body measuring 50 mm by 80 mm by 5 mm thick by the injection molding method at a cylinder temperature of 280° C. and a die temperature of 80° C. for a cycle time of 50 seconds, and a YI value of the molded body is measured with the spectrophotometer under conditions of a C light source and a two-degree field of view.

<12> A method of producing an optical molded article, comprising molding the polycarbonate resin composition of any one of Items <1> to <11> at a temperature of from 280° C. to 360° C.

<13> An optical molded article, which is obtained by the production method of Item <12>.

<14> The optical molded article according to Item <13>, wherein the optical molded article comprises a light-guiding member.

Advantageous Effects of Invention

According to the present invention, the polycarbonate resin composition that is not reduced in optical characteristics by its deterioration at the time of its molding even when molded in a wide temperature region, and the optical molded article using the composition can be provided.

DESCRIPTION OF EMBODIMENTS

Figure 1:
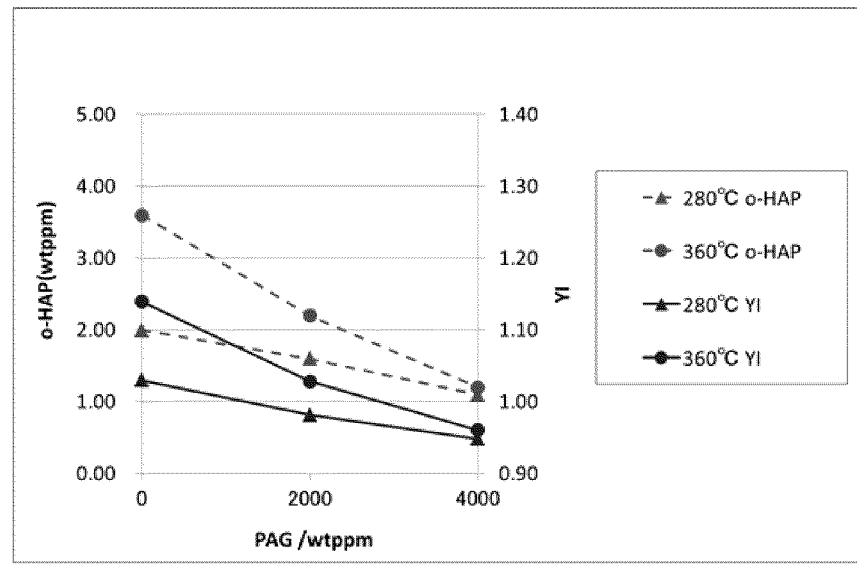
FIG. 1 is a graph for showing a relationship at the time of the molding of a polycarbonate resin composition according to the present invention among the YI value of a molded article, the production amount of o-hydroxyacetophenone to be produced, and the addition amount of a polyether added to the polycarbonate resin composition according to the present invention.

A polycarbonate resin composition of the present invention includes, with respect to 100 parts by mass of an aromatic polycarbonate resin (A), 0.005 part by mass to 1 part by mass of a specific phosphorus-based compound (B), and 0.005 part by mass to 5 parts by mass of a polyether compound (C) having a polyoxyalkylene structure.

The inventors of the present invention have found that combined use of the specific phosphorus-based compound (B) that has high heat resistance and is excellent in hydrolysis resistance and the polyether compound (C) can provide a polycarbonate resin composition that is not reduced in optical characteristics by its deterioration at the time of its molding even when molded in a wide temperature region. That is, when the specific phosphorus-based compound (B) and the polyether compound (C) are used in combination, the compounds can interact with each other to efficiently suppress a yellowing component produced from the polycarbonate resin by an influence of processing heat and its heat deterioration. As a result, even in the case of molding at a high temperature of more than 340° C., the composition can be molded without the impairment of its optical performance, and provides a molded body maintaining stable performance for a long time period.

[Component (A): Aromatic Polycarbonate Resin (A)]

A resin produced by a known method can be used as the aromatic polycarbonate resin (A) to be incorporated into the polycarbonate resin composition of the present invention without any particular limitation.

For example, a resin produced from a dihydric phenol and a carbonate precursor by a solution method (interfacial polycondensation method) or a melting method (ester exchange method), i.e., a resin produced by the interfacial polycondensation method involving causing the dihydric phenol and phosgene to react with each other in the presence of an end terminator, or by causing the dihydric phenol and diphenyl carbonate or the like to react with each other in the presence of the end terminator according to the ester exchange method or the like can be used.

Examples of the dihydric phenol may include various dihydric phenols, in particular, 2,2-bis(4-hydroxyphenyl) propane [bisphenol A], bis(4-hydroxyphenyl)methane, 1,1'-bis(4-hydroxyphenyl)ethane, 2,2-bis(4-hydroxy-3,5-dimethylphenyl)propane, 4, 4'-dihydroxydiphenyl, a bis(4-hydroxyphenyl)cycloalkane, bis(4-hydroxyphenyl) oxide, bis(4-hydroxyphenyl) sulfide, bis(4-hydroxyphenyl) sulfone, bis(4-hydroxyphenyl) sulfoxide, and bis(4-hydroxyphenyl) ketone. In addition, examples thereof can also include hydroquinone, resorcin, and catechol. One kind of those dihydric phenols may be used alone, or two or more kinds thereof may be used in combination. Among them, bis(hydroxyphenyl)alkane-based phenols are preferred, and bisphenol A is particularly suitable.

The carbonate precursor is, for example, a carbonyl halide, a carbonyl ester, or a haloformate, and is specifically phosgene, a dihaloformate of a dihydric phenol, diphenyl carbonate, dimethyl carbonate, diethyl carbonate, or the like.

The component (A) in the present invention may have a branched structure, and a branching agent may be, for example, 1,1,1-tris(4-hydroxyphenyl)ethane, a, a', a"-tris(4-hydroxyphenyl)-1,3,5-triisopropylbenzene, phloroglucin, trimellitic acid, or 1,3-bis(o-cresol).

A monovalent carboxylic acid or a derivative thereof or a monohydric phenol can be used as the end terminator. Examples thereof may include p-tertbutylphenol, p-phenylphenol, p-cumylphenol, p-perfluorononylphenol, p-(perfluorononylphenyl)phenol, p-(perfluorohexylphenyl)phenol, p-tert-perfluorobutylphenol, 1-(p-hydroxybenzyl)perfluorodecane, p-[2-(1H,1H-perfluorotridodecyloxy)-1,1,1,3,3,3-hexafluoropropyl]phenol, 3,5-bis(perfluorohexyloxycarbonyl)phenol, perfluorododecyl p-hydroxybenzoate, p-(1H,1H-perfluorooctyloxy)phenol, 2H,2H,9H-perfluorononanoic acid, and 1,1,1,3,3,3-hexafluoro-2-propanol.

It is preferred that the aromatic polycarbonate resin (A) includes a polycarbonate including, in a main chain thereof, a repeating unit represented by the following general formula (I):

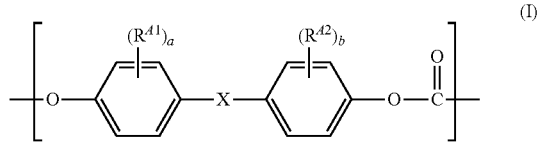

(I)

wherein $R^{A1}$ and $R^{A2}$ each independently represent an alkyl group or alkoxy group having 1 to 6 carbon atoms, and $R^{A1}$ and $R^{A2}$ may be identical to or different from each other, X represents a single bond, an alkylene group having 1 to 8 carbon atoms, an alkylidene group having 2 to 8 carbon atoms, a cycloalkylene group having 5 to 15 carbon atoms, a cycloalkylidene group having 5 to 15 carbon atoms, —S—, —SO—, —SO$_2$—, —O—, or —CO—, and a and b each independently represent an integer of from 0 to 4, when a represents 2 or more, $R^{A1}$'s may be identical to or different from each other, and when b represents 2 or more, $R^{A2}$'s may be identical to or different from each other.

Examples of the alkyl group represented by each of $R^{A1}$ and $R^{A2}$ include a methyl group, an ethyl group, a n-propyl group, an isopropyl group, various butyl groups (the term "various" means that a linear group and various branched groups are included, and the same holds true for the following), various pentyl groups, and various hexyl groups. An example of the alkoxy group represented by each of $R^{A1}$ and $R^{A2}$ is an alkoxy group whose alkyl group moiety is the alkyl group described above.

$R^{A1}$ and $R^{A2}$ each preferably represent an alkyl group having 1 to 4 carbon atoms or an alkoxy group having 1 to 4 carbon atoms.

Examples of the alkylene group represented by X include a methylene group, an ethylene group, a trimethylene group, a tetramethylene group, and a hexamethylene group. Among them, an alkylene group having 1 to 5 carbon atoms is preferred. Examples of the alkylidene group represented by X include an ethylidene group and an isopropylidene group. Examples of the cycloalkylene group represented by X include a cyclopentanediyl group, a cyclohexanediyl group, and a cyclooctanediyl group. Among them, a cycloalkylene group having 5 to 10 carbon atoms is preferred. Examples of the cycloalkylidene group represented by X include a cyclohexylidene group, a 3,5,5-trimethylcyclohexylidene group, and a 2-adamantylidene group. Among them, a cycloalkylidene group having 5 to 10 carbon atoms is preferred, and a cycloalkylidene group having 5 to 8 carbon atoms is more preferred.

a and b each independently represent an integer of from 0 to 4, preferably from 0 to 2, more preferably 0 or 1.

In the present invention, the aromatic polycarbonate resin (A) preferably contains a polycarbonate resin having a bisphenol A structure from the viewpoints of, for example, the transparency, mechanical characteristics, and thermal characteristics of a molded body to be obtained. The polycarbonate resin having a bisphenol A structure is specifically, for example, such a resin that X in the general formula (I) represents an isopropylidene group. The content of the polycarbonate resin having a bisphenol A structure in the aromatic polycarbonate resin (A) is preferably from 50 mass % to 100 mass %, more preferably from 75 mass % to 100 mass %, still more preferably from 85 mass % to 100 mass %.

In the present invention, the viscosity-average molecular weight (Mv) of the component (A) is preferably from 9,000 to 50,000, more preferably from 10,000 to 30,000, still more preferably from 11,000 to 25,000 from the viewpoint of the flowability. In particular, when the polycarbonate resin composition of the present invention is used as a thin-walled optical molded article, such as a light-guiding plate, the Mv of the aromatic polycarbonate resin (A) is preferably from 9,000 to 17,000.

In the present invention, the viscosity-average molecular weight (Mv) is calculated from the following Schnell's equation after the determination of a limiting viscosity [η] through the measurement of the viscosity of a methylene chloride solution (concentration: g/l) at 20° C. with an Ubbelohde-type viscometer.

$$[\eta] = 1.23 \times 10^{-5} Mv^{0.83}$$

[Component (B): Phosphorus-Based Compound (B) Having Aryl Group]

The phosphorus-based compound (B) to be incorporated into the polycarbonate resin composition of the present invention is such a compound that the amount of a compound having a phenol structure produced by the decomposition of the compound 1,500 hours after its standing under the conditions of 40° C. and a humidity of 90% is 5 mass % or less, preferably 3 mass % or less, more preferably 1 mass % or less, particularly preferably 0.5 mass % or less with respect to the phosphorus-based compound (B). That is, the phosphorus-based compound (B) to be used in the present invention is excellent in hydrolysis resistance and produces a small amount of the compound having a phenol structure. The amount of the compound having a phenol structure can be determined with a gas chromatograph, and more specifically, is measured by a method to be described in Examples.

When the weight of the phosphorus-based compound (B) to be incorporated into the polycarbonate resin composition of the present invention is measured with a thermogravimetric-differential thermal analysis (TG-DTA) machine under a nitrogen atmosphere, the temperature at which the weight becomes smaller than the weight before the measurement by 2% is 340° C. or more.

Here, the temperature at which the weight becomes smaller by 2% is preferably 345° C. or more, more preferably 350° C. or more.

Although a conventional phosphite-based antioxidant having a pentaerythritol diphosphite structure exhibits a satisfactory antioxidant action at a normal processing temperature of a polycarbonate resin, the antioxidant thermally decomposes at a high temperature of more than 340° C. to abruptly lose its antioxidant action. Further, the antioxidant produces a product responsible for yellowing by itself owing to the thermal decomposition, and hence its insufficient heat resistance is a problem. In addition, many of the phosphite-based antioxidants are liable to hydrolyze, and in the moist heat resistance test of a light-guiding plate, an antioxidant in the light-guiding plate is liable to hydrolyze to cause the following problem: the light-guiding plate discolors or becomes opaque owing to an influence of the hydrolysate. In WO 2013/088796 A1, there is a disclosure that a specific diphosphite-based antioxidant typified by bis(2,4-dicumylphenyl)pentaerythritol diphosphite is effective as an antioxidant capable of satisfying both required characteristics, i.e., heat resistance and hydrolysis resistance.

However, the method of WO 2013/088796 A1 requires an alicyclic epoxy compound from the viewpoint of the moist heat resistance of the light-guiding plate. In addition, in the method, sufficient performance cannot be expressed in the molding temperature region of less than 300° C., though excellent heat stability in high-temperature molding is obtained.

The inventors of the present invention have found that the use of the specific phosphorus-based compound (B) in combination with the polyether compound (C) can provide a polycarbonate resin composition that is not reduced in optical characteristics by its deterioration at the time of its molding even when molded in a wide temperature region.

The phosphorus-based compound (B) to be used in the present invention is preferably a phosphorus-based compound having a phosphite structure, more preferably a pentaerythritol diphosphite compound represented by the following general formula (II):

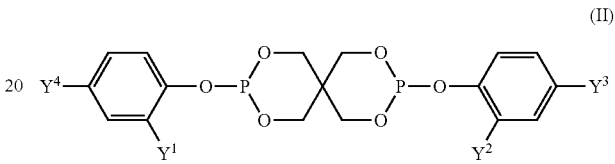

wherein $Y^1$ to $Y^4$ each represent a hydrocarbon group having 6 to 15 carbon atoms, and may be identical to or different from each other. In addition, $Y^1$ to $Y^4$ each independently preferably represent a cumyl group that may be unsubstituted or substituted, a phenyl group that may be unsubstituted or substituted, a naphthyl group that may be unsubstituted or substituted, or a biphenyl group that may be unsubstituted or substituted.

The phosphorus-based compound (B) to be used in the present invention is preferably a pentaerythritol diphosphite compound represented by the following general formula (II-1):

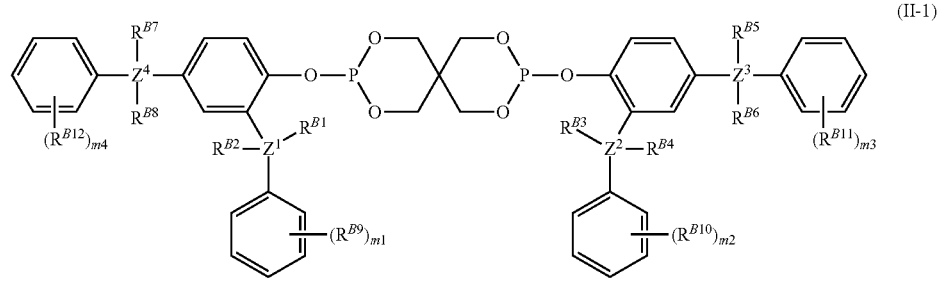

wherein $R^{B1}$ to $R^{B8}$ each represent an alkyl group or an alkenyl group, and may be identical to or different from each other, and $R^{B1}$ and $R^{B2}$, $R^{B3}$ and $R^{B4}$, $R^{B5}$ and $R^{B6}$, or $R^{B7}$ and $R^{B8}$ may be bonded to each other to form a ring, $R^{B9}$ to $R^{B12}$ each represent a hydrogen atom or an alkyl group, and may be identical to or different from each other, m1 to m4 each represent an integer of from 0 to 5, and may be identical to or different from each other, and $Z^1$ to $Z^4$ each represent a single bond or a carbon atom, and may be identical to or different from each other, and when $Z^1$ to $Z^4$ each represent a single bond, $R^{B1}$ to $R^{B8}$ are excluded from the general formula (II-1). $R^{B1}$ to $R^{B8}$ each have preferably 1 or more and 5 or less carbon atoms, more preferably 1 or more and 3 or less carbon atoms, most preferably 1 carbon atom. $R^{B9}$ to $R^{B12}$ each preferably represent a hydrogen atom. m1 to m4 each represent preferably from 0 to 3, more preferably from 0 to 1, most preferably 0. $Z^1$ to $Z^4$ each preferably represent a carbon atom.

The pentaerythritol diphosphite compound represented by the general formula (II) or (II-1) can be obtained by adding a chlorine-based solvent to phosphorus trichloride and pentaerythritol to provide pentaerythritol dichlorophosphite, and then heating and mixing the contents in the presence of an aromatic solvent and an organic nitrogen-containing basic compound (see, for example, JP 2004-018406 A).

Among the pentaerythritol diphosphite compounds each represented by the general formula (II) or (II-1), bis(2,4-dicumylphenyl)pentaerythritol diphosphite represented by the following general formula (II-2) is particularly suitable because the compound can satisfactorily impart heat resistance and hydrolysis resistance to the polycarbonate resin composition, and is easily available. The compound is available as a commercial product, and for example, "Doverphos (trademark) S-9228PC" manufactured by Dover Chemical Corporation can be used.

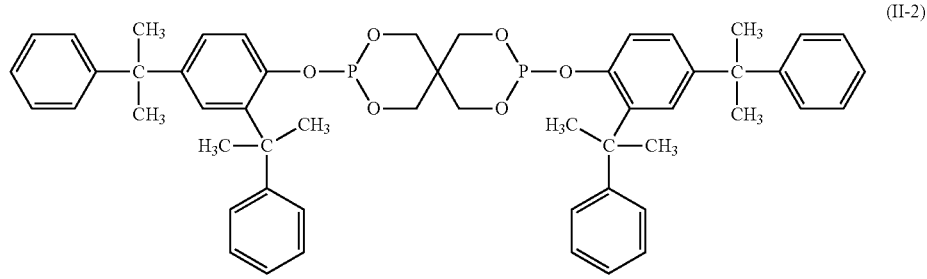 [SMILES: CC(C)(c1ccccc1)c1ccc(OP2OCC3(CO2)COP(Oc2ccc(C(C)(C)c4ccccc4)cc2C(C)(C)c2ccccc2)OC3)c(C(C)(C)c2ccccc2)c1]

(II-2)

With regard to the heat resistance of a normal pentaerythritol diphosphite compound, its 98% retention temperature measured with a thermogravimetric-differential thermal analysis (TG-DTA) machine under a nitrogen atmosphere is from about 240° C. to about 280° C. In contrast, the 98% retention temperature of bis(2,4-dicumylphenyl)pentaerythritol diphosphite represented above is 340° C. or more. The compound has such heat resistance, and hence its performance is not impaired even in the case of molding at a high temperature of more than 340° C. On the contrary, its antioxidant action tends to be activated in the case of the high-temperature molding.

The hydrolysis of a polycarbonate resin molded body is caused mainly by liberated phenol and phosphoric acid produced by the hydrolysis of a phosphorus-based antioxidant in the molded body. Accordingly, when a phosphorus-based antioxidant whose hydrolysis easily advances is used, the polycarbonate molded body itself hydrolyzes to undergo a reduction in molecular weight and opacification.

The amount of each of liberated phenol and phosphoric acid produced by the hydrolysis of the phosphorus-based compound (B) to be used in the present invention 1,500 hours after the standing thereof under the conditions of 40° C. and a humidity of 90% was 1/100 or less of that in the case of a conventional pentaerythritol diphosphite structure. The compound is excellent in hydrolysis resistance as described above, and hence even when the compound is used after having been stored for a long time period, no hydrolysate enters a molded body, and the hydrolysis of the compound hardly occurs even after its blending into the molded body. Accordingly, a molded body using the polycarbonate resin composition blended with the phosphorus-based compound (B) can be stably used for a long time period without any reductions in optical characteristics thereof.

The content of the phosphorus-based compound (B) in the polycarbonate resin composition of the present invention is from 0.005 part by mass to 1 part by mass, preferably from 0.01 part by mass to 0.8 part by mass, more preferably from 0.03 part by mass to 0.5 part by mass, still more preferably from 0.03 part by mass to 0.3 part by mass with respect to 100 parts by mass of the aromatic polycarbonate resin (A) from the viewpoint that a polycarbonate resin composition that is not reduced in optical characteristics by its deterioration at the time of its molding even when molded in a wide temperature region is obtained.

[Component (C): Polyether Compound (C) Having Polyoxyalkylene Structure]

The polyether compound (C) having a polyoxyalkylene structure to be incorporated into the polycarbonate resin composition of the present invention is represented by the following formula (1):

$$R^{C3}O—(R^{C1}O)_m(R^{C2}O)_n—R^{C4} \quad (1)$$

wherein $R^{C1}$ and $R^{C2}$ each represent an alkylene group having 1 or more carbon atoms, and $R^{C1}$ and $R^{C2}$ may be identical to or different from each other, m+n represents 5 or more and less than 300, when m represents 2 or more, $R^{C1}$'s may be identical to or different from each other, and when n represents 2 or more, $R^{C2}$'s may be identical to or different from each other, and $R^{C3}$ and $R^{C4}$ each represent a hydrogen atom, a hydrocarbon group having 1 to 30 carbon atoms, an alkanoyl group having 1 to 30 carbon atoms, an alkenoyl group having 2 to 30 carbon atoms, or a glycidyl group, and $R^{C3}$ and $R^{C4}$ may be identical to or different from each other.

$R^{C1}$ and $R^{C2}$ each have preferably 1 to 8, more preferably 1 to 6, still more preferably 1 to 5, most preferably 2 to 5 carbon atoms. Examples thereof may include a methylene group, an ethylene group, a trimethylene group, a propylene group, a tetramethylene group, and a hexamethylene group.

A polyoxyalkylene group represented by $(R^{C1}O)_m$ is not limited to a group having a single oxyalkylene unit as a repeating unit, such as a polyoxyethylene group or a polyoxypropylene group, and may be a group having a plurality of oxyalkylene units different from each other in number of carbon atoms, such as an oxyethylene unit and an oxypropylene unit, as repeating units.

A polyoxyalkylene group represented by $(R^{C2}O)_n$ is not limited to a group having a single oxyalkylene unit as a repeating unit, such as a polyoxyethylene group or a polyoxypropylene group, and may be a group having a plurality of oxyalkylene units different from each other in number of carbon atoms, such as an oxyethylene unit and an oxypropylene unit, as repeating units.

Examples of the hydrocarbon group having 1 to 30 carbon atoms represented by each of $R^{C3}$ and $R^{C4}$ include an alkyl group having 1 to 30 carbon atoms, an alkenyl group having 2 to 30 carbon atoms, an aryl group having 6 to 30 carbon atoms, and an aralkyl group having 7 to 30 carbon atoms.

Each of the alkyl group and the alkenyl group may be linear, branched, or cyclic. Examples thereof include a methyl group, an ethyl group, a n-propyl group, an isopropyl group, various butyl groups, various pentyl groups, various hexyl groups, various octyl groups, a cyclopentyl group, a cyclohexyl group, an allyl group, a propenyl group, various butenyl groups, various hexenyl groups, various octenyl groups, a cyclopentenyl group, and a cyclohexenyl group. Examples of the aryl group include a phenyl group, a tolyl group, and a xylyl group. Examples of the aralkyl group include a benzyl group, a phenethyl group, and a methylbenzyl group.

The alkanoyl group having 1 to 30 carbon atoms represented by each of $R^{C3}$ and $R^{C4}$ may be linear or branched, and examples thereof include a methanoyl group, an ethanoyl group, a n-propanoyl group, an isopropanoyl group, a n-butanoyl group, a t-butanoyl group, a n-hexanoyl group, a n-octanoyl group, a n-decanoyl group, a n-dodecanoyl group, and a benzoyl group. Among them, an alkanoyl group having 1 to 20 carbon atoms is preferred from the viewpoints of the compatibility, heat stability, and ease of production of the composition.

The alkenoyl group having 2 to 30 carbon atoms represented by each of $R^{C3}$ and $R^{C4}$ may be linear or branched, and examples thereof include an ethenoyl group, a n-propenoyl group, an isopropenoyl group, a n-butenoyl group, a t-butenoyl group, a n-hexenoyl group, a n-octenoyl group, a n-decenoyl group, and a n-dodecenoyl group. Among them, an alkenoyl group having 2 to 10 carbon atoms is preferred, and an alkenoyl group having 2 to 6 carbon atoms is more preferred from the viewpoint that the molecular weight of the composition is reduced, from the viewpoints of its compatibility and solubility, and from the viewpoint of its ease of production.

The polyether compound (C) having a polyoxyalkylene structure represented by the general formula (1) is preferably a polyoxyalkylene glycol in which in the formula (1), $R^{C1}$ and $R^{C2}$ each represent an alkylene group having 2 to 5 carbon atoms, and $R^{C3}$ and $R^{C4}$ each represent a hydrogen atom.

In addition, specific examples of the polyether compound (C) having a polyoxyalkylene structure represented by the general formula (1) include a polyethylene glycol, a polypropylene glycol, a polytetramethylene glycol, a polyoxyethylene-polyoxypropylene glycol, a polyoxyethylene-polyoxytetramethylene glycol, a polyoxypropylene-polyoxytetramethylene glycol, a polyoxyethylene monomethyl ether, a polyoxyethylene dimethyl ether, a polyoxyethylene-bisphenol A ether, a polyoxypropylene-bisphenol A ether, a polyoxyethylene-polyoxypropylene-bisphenol A ether, a polyethylene glycol-allyl ether, a polyethylene glycol-diallyl ether, a polypropylene glycol-allyl ether, a polypropylene glycol-diallyl ether, a polyethylene glycol-polypropylene glycol-allyl ether, a polyethylene glycol dimethacrylate, a polypropylene glycol dimethacrylate, and a polypropylene glycol distearate.

Those compounds are available as commercial products, and for example, "UNIOX (trademark)", "UNIOL (trademark)", "UNILUB (trademark)", "UNISAFE (trademark)", "POLYCERIN (trademark)", or "EPIOL (trademark)", which is manufactured by NOF Corporation, can be used.

Among them, a UNILUB DE series of a random copolymerization type of a polyoxyethylene glycol and a polyoxypropylene glycol, a POLYCERIN DC series of a random copolymerization type of a polyoxyethylene glycol and a polyoxytetramethylene glycol, or a POLYCERIN DCB series of a random copolymerization type of a polyoxypropylene glycol and a polyoxytetramethylene glycol, the series each having a molecular weight of from 1,000 to 5,000, is particularly preferred.

In, for example, JP 4069364 B2, as related art, there is a disclosure that the addition of a polyoxyalkylene glycol improves the light transmittance of a polycarbonate resin. A polyoxyalkylene glycol formed of an alkyl group having 1 to 3 carbon atoms, or a derivative formed of the glycol and a specific aliphatic compound is used as the polyoxyalkylene glycol to be used in the technical contents. A polyoxyethylene glycol or a polyoxypropylene glycol is a hydrophilic polymer and has high compatibility with a polycarbonate resin because any such glycol is a polyoxyalkylene glycol of an alkyl group having a small number of carbon atoms. On the other hand, however, any such glycol has low heat resistance and hence involves the following drawbacks: when a polycarbonate resin having added thereto the glycol is molded at a temperature of more than 320° C., its hue reduces to reduce its luminance and light transmittance; and when the resin is molded at a temperature of more than 340° C., the resin cannot be used as a light-guiding material owing to the occurrence of a silver by its decomposition gas. The inventors of the present invention have found that, through the use of the polyether compound (C) in combination with the specific phosphorus-based compound (B), a silver due to deterioration at the time of molding is prevented from occurring even when molding is performed in a wide temperature region, and a polycarbonate resin composition that is not reduced in optical characteristics can be provided.

A general polyether compound starts to decompose at more than 250° C., and the decomposition becomes vigorous at more than 300° C. Accordingly, vigorous thermal decomposition of the compound is assumed to occur at a molding temperature of more than 340° C. to be responsible for the occurrence of a silver. Meanwhile, a general phosphorus-based antioxidant also thermally decomposes at a molding temperature of more than 340° C. to lose its antioxidant action. When the antioxidant itself thermally decomposes, the antioxidant serves as a cause for a silver or a product responsible for yellowing.

The specific phosphorus-based compound (B) to be used in the polycarbonate resin composition of the present invention has high heat resistance, and maintains its antioxidant action even at a molding temperature of more than 340° C. without thermally decomposing. The maintenance of the antioxidant action suppresses the thermal decomposition of the polyether compound, and hence prevents a silver from occurring.

The optical characteristics are transparency and a color tone, a YI value is used in a typical evaluation for the color tone. The inventors have analyzed and searched a product responsible for yellowing, which reduces the color tone in high-temperature molding, over a long time period, and as a result, have found that a product responsible for yellowing derived from the polycarbonate resin is produced by melt kneading and an injection molding process. A mechanism for the foregoing is as follows: in the kneading and the molding process, a substance called o-hydroxyacetophenone is produced by the oxidation of components derived from a polycarbonate molecule and an oligomer molecule, and the substance is thermally modified to become a yellowed product, thereby causing a reduction in color tone.

Under molding at a temperature as low as 280° C., the production of o-hydroxyacetophenone is moderate and is suppressed even by an antioxidant, and hence the color tone is relatively satisfactory. However, at a molding temperature of more than 340° C., o-hydroxyacetophenone is produced in a large amount and hence the production cannot be suppressed by the antioxidant.

The inventors of the present invention have considered that the reduction in color tone is suppressed by suppressing the production of o-hydroxyacetophenone derived from the polycarbonate resin and serving as a product responsible for the reduction in color tone, and have made extensive investigations. As a result, the inventors have found that the production of o-hydroxyacetophenone can be efficiently suppressed by using the specific phosphorus-based compound (B) and the polyether compound (C) in combination, and thus have completed the present invention. That is, the inventors have found that the combined use of the specific phosphorus-based compound (B) and the polyether compound (C) exhibits a special interaction, and hence as compared with the case where any other phosphorus-based antioxidant and the polyether compound are added in combination, the deterioration of the color tone is substantially prevented from occurring from a low-temperature molding region to a high-temperature molding region of more than 340° C., and a stable color tone and the transparency can be maintained. Thus, the inventors have completed the polycarbonate resin composition. The foregoing action is specifically shown in FIG. 1.

An example of the polycarbonate resin composition in which 100 parts by weight of "TARFLON FN1500" (manufactured by Idemitsu Kosan Co., Ltd., bisphenol A polycarbonate resin, viscosity-average molecular weight (Mv)=14,500) serving as the polycarbonate resin, 0.05 part by mass of "Doverphos S-9228PC" (manufactured by Dover Chemical Corporation, bis(2,4-dicumylphenyl)pentaerythritol diphosphite) serving as the specific phosphorus-based compound (B), and 0.0 parts by mass to 0.4 part by mass of "UNILUB DE50-25" (manufactured by NOF Corporation, polyoxyethylene glycol-polyoxypropylene glycol) serving as the polyether compound (C) are used in combination is shown in FIG. 1.

Figure 2:
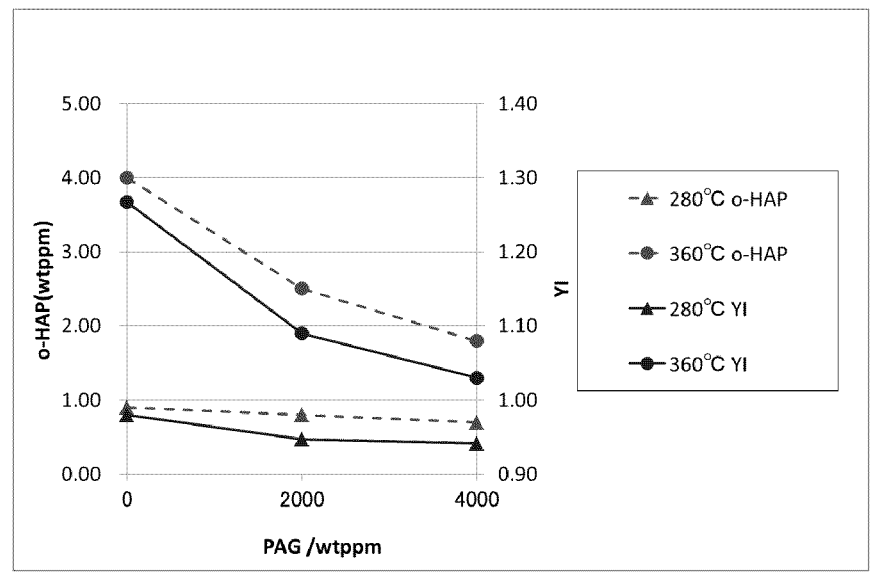
FIG. 2 is a graph for showing a relationship at the time of the molding of a polycarbonate resin composition containing a phosphorus-based compound to be generally used among the YI value of a molded article, the production amount of o-hydroxyacetophenone to be produced, and the addition amount of a polyether added to the polycarbonate resin composition containing the phosphorus-based compound to be generally used.

An example having the same composition as that of FIG. 1 except that the phosphorus-based compound is changed to "ADK STAB PEP-36" (manufactured by ADEKA Corporation, bis(2,6-di-tert-butyl-4-methylphenyl)pentaerythritol diphosphite) serving as a general phosphorus-based compound is shown in FIG. 2.

The terms "o-HAP" and "PAG" shown in the figures represent o-hydroxyacetophenone and the polyether, respectively.

In FIG. 1, it is found that when the polycarbonate resin composition is molded, as the addition amount of the polyether increases, both the YI value of a molded article and the amount of o-hydroxyacetophenone to be produced at the time of the molding reduce, and a difference between the YI values of the molded articles at 280° C. and 360° C. is substantially eliminated.

Meanwhile, also in FIG. 2, when the polycarbonate resin composition is molded, as the addition amount of the polyether increases, both the YI value of a molded article and the amount of o-hydroxyacetophenone to be produced at the time of the molding reduce. However, a difference in YI value and a difference in amount of o-hydroxyacetophenone, between the molded articles at 280° C. and 360° C. remain large irrespective of the addition amount of the polyether.

The polyether cannot be added in a large amount because the polyether causes reductions in physical properties of the polycarbonate resin. In addition, in the case of a general antioxidant, thermal decomposition at high temperature or a reduction in hydrolysis resistance occurs, and hence it is difficult to improve the performance of the composition through an increase in amount of the antioxidant. As can be seen the foregoing, an improvement in color tone at the time of high-temperature molding merely through the blending of the general antioxidant and the polyether has its limit.

The number-average molecular weight (Mn) of the polyether compound (C), which is not particularly limited, is preferably from 200 to 10,000, more preferably from 500 to 8,000, still more preferably from 1,000 to 5,000.

The content of the polyether compound (C) in the polycarbonate resin composition of the present invention is from 0.005 part by mass to 5 parts by mass, preferably from 0.05 part by mass to 2 parts by mass, more preferably from 0.1 part by mass to 1 part by mass with respect to 100 parts by mass of the aromatic polycarbonate resin (A) from the viewpoint that a polycarbonate resin composition that is not reduced in optical characteristics by its deterioration at the time of its molding even when molded in a wide temperature region is obtained.

[Additive]

In addition to the components (A) to (C), any additive, such as a polyorganosiloxane, may be appropriately added to the polycarbonate resin composition of the present invention.

The polyorganosiloxane is preferably a compound having one or more kinds of functional groups, such as an alkoxy group, an aryloxy group, a polyoxyalkylene group, a carboxyl group, a silanol group, an amino group, a mercapto group, an epoxy group, and a vinyl group.

The addition amount of the polyorganosiloxane is preferably from 0.01 part by mass to 0.15 part by mass, more preferably from 0.02 part by mass to 0.15 part by mass, still more preferably from 0.05 part by mass to 0.1 part by mass with respect to 100 parts by mass of the aromatic polycarbonate resin (A). When the addition amount falls within the range, the polyorganosiloxane can concert with any other component to improve the releasability of the composition. Further, even under a molding condition at a high temperature of more than 340° C., in particular, a continuous molding condition, the occurrence of a silver and the amount of a mold deposit can be significantly reduced.

The viscosity of the polyorganosiloxane at 25° C. is preferably 10 $mm^2/s$ or more from the viewpoint of a lubricating effect serving as the releasability, and is preferably 200 $mm^2/s$ or less from the viewpoint of its dispersibility in the polycarbonate resin. From the viewpoints, the viscosity of the polyorganosiloxane falls within the range of more preferably from 20 $mm^2/s$ to 150 $mm^2/s$, still more preferably from 40 $mm^2/s$ to 120 $mm^2/s$.

A difference between the refractive index of the polyorganosiloxane and the refractive index of a polycarbonate is preferably made as small as possible in order that the transparency of the polycarbonate may not be reduced at the time of the addition of the polyorganosiloxane thereto. The refractive index of the polyorganosiloxane is preferably 1.45 or more, more preferably 1.50 or more, still more preferably 1.52 or more because the refractive index of the polycarbonate is 1.58.

[Aromatic Polycarbonate Resin Composition and Optical Molded Article]

A method of producing the polycarbonate resin composition of the present invention is not particularly limited.

For example, the components (A) to (C), and as required, the additive are mixed, and the mixture is melted and kneaded. The melting and kneading can be performed by a typically used method, for example, a method using a ribbon blender, a Henschel mixer, a Banbury mixer, a drum tumbler, a single-screw extruder, a double-screw extruder, a co-kneader, a multiple-screw extruder, or the like. In normal cases, a heating temperature at the time of the melting and kneading is appropriately selected from the range of from about 220° C. to about 300° C.

The polycarbonate resin composition of the present invention can be produced by using the melt-kneaded product or the resultant resin pellet as a raw material through the application of a known molding method, such as a hollow molding method, an injection molding method, an injection compression molding method, an extrusion molding method, a vacuum molding method, a blow molding method, a press molding method, an air-pressure molding method, an expansion molding method, a heat bending molding method, a compression molding method, a calender molding method, or a rotational molding method.

The polycarbonate resin composition of the present invention is suitable for a molding method requiring a molding material to have high flowability, such as the injection molding method, because the composition is improved in a heat resistance that has heretofore been insufficient and hence can resist molding at a high temperature of more than 340° C. Meanwhile, in the extrusion molding method, a product having high optical characteristics, such as a sheet or a film, the product having high transparency and being free from yellowing, can be obtained by molding the composition at a low temperature of from about 220° C. to about 280° C.

In the polycarbonate resin composition according to the present invention, it is preferred that the amount of o-hydroxyacetophenone measured by the following measurement method (2) be 2.0 ppm by mass or less, and the amount of o-hydroxyacetophenone measured by the following measurement method (1) be twice or less as large as the amount of o-hydroxyacetophenone measured by the measurement method (2).

It is more preferred that the amount of o-hydroxyacetophenone measured by the following measurement method (1) be 1.5 times or less as large as the amount of o-hydroxyacetophenone measured by the measurement method (2), and be 3.0 ppm by mass or less.

Further, it is preferred to adjust the specific phosphorus-based compound (B) and the polyether compound (C) so that the amount of o-hydroxyacetophenone measured by the following measurement method (2) may be 1.5 ppm by mass or less, and the amount of o-hydroxyacetophenone measured by the following measurement method (1) may be 1.2 times or less as large as the amount of o-hydroxyacetophenone measured by the measurement method (2).

Measurement Method (1)

A polycarbonate resin molding material is pelletized, followed by drying, and is then molded into a molded body measuring 50 mm by 80 mm by 5 mm thick by an injection molding method at a cylinder temperature of 360° C. and a die temperature of 80° C. for a cycle time of 50 seconds, the molded body is pulverized and dissolved in chloroform, and the amount of o-hydroxyacetophenone in the solution is determined by high-performance liquid chromatography.

Measurement Method (2)

The polycarbonate resin molding material is pelletized, followed by drying, and is then molded into a molded body measuring 50 mm by 80 mm by 5 mm thick by the injection molding method at a cylinder temperature of 280° C. and a die temperature of 80° C. for a cycle time of 50 seconds, the molded body is pulverized and dissolved in chloroform, and the amount of o-hydroxyacetophenone in the solution is determined by the high-performance liquid chromatography.

In the polycarbonate resin composition according to the present invention, it is preferred that YI values measured by the following measurement methods (3) and (4) be 1.2 or less, and a difference between the YI values measured by the methods (3) and (4) be 0.1 or less.

In the polycarbonate resin composition according to the present invention, it is more preferred that the YI values measured by the following measurement methods (3) and (4) be 1.15 or less, and the difference between the YI values measured by the methods (3) and (4) be 0.08 or less. In the polycarbonate resin composition according to the present invention, it is still more preferred that the YI values measured by the following measurement methods (3) and (4) be 1.1 or less, and the difference between the YI values measured by the methods (3) and (4) be 0.05 or less.

Measurement Method (3)

A polycarbonate resin molding material is pelletized, followed by drying, and is then molded into a molded body measuring 50 mm by 80 mm by 5 mm thick by an injection molding method at a cylinder temperature of 360° C. and a die temperature of 80° C. for a cycle time of 50 seconds, and the YI value of the molded body is measured with a spectrophotometer under conditions of a C light source and a two-degree field of view.

Measurement Method (4)

The polycarbonate resin molding material is pelletized, followed by drying, and is then molded into a molded body measuring 50 mm by 80 mm by 5 mm thick by the injection molding method at a cylinder temperature of 280° C. and a die temperature of 80° C. for a cycle time of 50 seconds, and the YI value of the molded body is measured with the spectrophotometer under conditions of a C light source and a two-degree field of view.

The polycarbonate resin composition of the present invention is a resin composition excellent in light transmittance and luminance, and capable of resisting molding at high temperature, and is particularly suitable for injection molding. Meanwhile, the composition has high low-temperature molding suitability. Accordingly, the composition can provide a molded article excellent in light transmission property in molding except the injection molding as well, and is hence useful as an optical molded article, in particular, a light-guiding member.

The polycarbonate resin composition of the present invention can be stably molded in a wide temperature range as described above, and can provide an optical molded article by being molded at a temperature of preferably from 280° C. to 360° C.

The light-guiding plate is not particularly limited and may be a flat plate having a thickness of from several millimeters to several hundreds of micrometers, or may be a curved plate or prism transfer plate having a lens effect. A molding method therefor is also not particularly limited, and the shape of, and the molding method for, the plate only need to be appropriately selected in accordance with purposes and applications.

EXAMPLES

The present invention is described more specifically by way of Examples below, but the present invention is not limited to these Examples.

[Measurement of Viscosity-average Molecular Weight (Mv)]

A viscosity-average molecular weight was calculated from the following Schnell's equation after the determination of a limiting viscosity [η] through the measurement of the viscosity of a methylene chloride solution (concentration: g/l) at 20° C. with an Ubbelohde-type viscometer.

$$[\eta]=1.23\times10^{-5}Mv^{0.83}$$

[Thermogravimetric-differential Thermal Analysis (TG-DTA) of Phosphorus-based Compound]

10 mg to 15 mg of a phosphorus-based compound was sampled, and its weight change at the time of a temperature increase up to 550° C. at a rate of temperature increase of 20° C./min under a nitrogen atmosphere was measured and recorded at each temperature with a thermogravimetric-differential thermal analysis machine TG/DTA Model 7200 manufactured by SII. An initial weight was defined as 100%, and the temperature at which the weight reduced by 2% was observed and defined as a 98% retention temperature.

[Hydrolysis Resistance Test of Phosphorus-based Compound]

A phosphorus-based compound was left to stand under the conditions of 40° C. and a humidity of 90% for 1,500 hours. After that, the mass of a compound having a phenol structure produced by its decomposition was determined with a gas chromatograph apparatus "GC-2014" manufactured by Shimadzu Corporation, and the ratio of the compound to the phosphorus-based compound was measured.

Components used in Examples and Comparative Examples are as described below.

<Aromatic Polycarbonate Resin (A)>
(A1): "TARFLON FN1500" (manufactured by Idemitsu Kosan Co., Ltd., bisphenol A polycarbonate resin, viscosity-average molecular weight (Mv)=14,500)
(A2): "TARFLON FN1200" (manufactured by Idemitsu Kosan Co., Ltd., bisphenol A polycarbonate resin, viscosity-average molecular weight (Mv)=11,500)

<Phosphorus-based Compound (B)>
(B1): "Doverphos S-9228PC" (manufactured by Dover Chemical Corporation, bis(2,4-dicumylphenyl)pentaerythritol diphosphite, produced 0.15 mass % of dicumylphenol after the hydrolysis resistance test)
(B2): "ADK STAB 2112" (manufactured by ADEKA Corporation, tris(2,4-di-tert-butylphenyl) phosphite, produced 6 mass % of 2,4-di-tert-butylphenol after the hydrolysis resistance test)
(B3): "ADK STAB PEP-36" (manufactured by ADEKA Corporation, bis(2,6-di-tert-butyl-4-methylphenyl)pentaerythritol diphosphite, produced 45 mass % of 2,6-di-tert-butyl-4-methylphenol after the hydrolysis resistance test)

<Polyether Compound (C)>
(C1): "POLYCERIN DC-1100" (manufactured by NOF Corporation, polyoxytetramethylene glycol-polyoxyethylene glycol)
(C2): "POLYCERIN DC-1800E" (manufactured by NOF Corporation, polyoxytetramethylene glycol-polyoxyethylene glycol)
(C3): "UNIOX GT-20IS" (manufactured by NOF Corporation, polyoxyethylene-triisostearic acid)
(C4): "UNILUB 50DE-25" (manufactured by NOF Corporation, polyoxyethylene glycol-polyoxypropylene glycol)
(C5): "EPIOL E-1000" (manufactured by NOF Corporation, polyethylene glycol diglycidyl ether)
(C6): "UNISAFE NKL-9520" (manufactured by NOF Corporation, polypropylene glycol distearate)
(C7): "PEG-6000J" (manufactured by Lion Corporation, polyethylene glycol)

<Other Additive>
"KR-511" (manufactured by Shin-Etsu Chemical Co., Ltd., polyorganosiloxane compound)
"CELLOXIDE 2021P" (manufactured by Daicel Corporation, 3,4-epoxycyclohexylmethyl-3',4'-epoxycyclohexanecarboxylate)

Examples 1 to 12 and Comparative Examples 1 to 8

In each example, a polycarbonate resin composition was prepared by blending respective components at amount ratios shown in Table 1. The polycarbonate resin composition was melted and kneaded with a vented single screw extruder having a screw diameter of 40 mm ("VS-40" manufactured by Tanabe Plastics Machinery Co., Ltd.) at a cylinder temperature of 250° C., and the melt-kneaded product was subjected to strand cutting to provide a pellet. The resultant pellet was dried at 110° C. for 5 hours, and was then molded into a flat plate-like test piece measuring 50 mm by 80 mm by 5 mm thick with an injection molding machine ("ES 1000" manufactured by Nissei Plastic Industrial Co., Ltd.) set to a cylinder temperature of 280° C. or 360° C. and a die temperature of 80° C. for a cycle time of 50 seconds.

In addition, a moist heat resistance test was performed as described below. Molding into a flat plate test piece measuring 40 mm by 80 mm by 3 mm thick was performed with an injection molding machine ("EC40N" manufactured by Toshiba Machine Co., Ltd.) at 350° C. for a cycle time of 30 seconds. The flat plate test piece was placed in a thermohygrostat available under the model name "LH33-12P" from Nagano Science Co., Ltd. set to a temperature of 85° C. and a relative humidity of 95% for 500 hours.

The YI value of the test piece obtained above was measured with a spectrophotometer ("U-4100" manufactured by Hitachi High-Technologies Corporation) under the conditions of a C light source and a two-degree field of view. The result is shown in Table 1. Acceptance criteria in a 5-millimeter test piece are as follows: the YI value of a test piece molded at 280° C. (molding at 280° C.) is 1.10 or less, and the YI value of a test piece molded at 360° C. (molding at 360° C.) is 1.25 or less. Although a YI value after the moist heat resistance test is not particularly limited, a difference ΔYI between the YI values before and after the test is required to be 0.2 or less.

In each of Examples 1 to 12 and Comparative Examples 1 to 8, the amount of o-hydroxyacetophenone was measured by each of the following measurement methods.

Measurement Method (1)

As described above, in each example, a pellet was obtained, followed by drying (110° C., 5 hours), and was then molded into a test piece measuring 50 mm by 80 mm by 5 mm thick by an injection molding method at a cylinder temperature of 360° C. and a die temperature of 80° C. for a cycle time of 50 seconds. The molded body was pulverized and dissolved in chloroform, and the amount of o-hydroxyacetophenone in the solution was determined by high-performance liquid chromatography.

Measurement Method (2)

As described above, in each example, a pellet was obtained, followed by drying (110° C., 5 hours), and was then molded into the above-mentioned test piece measuring 50 mm by 80 mm by 5 mm thick by the injection molding method at a cylinder temperature of 280° C. and a die temperature of 80° C. for a cycle time of 50 seconds. The molded body was pulverized and dissolved in chloroform, and the amount of o-hydroxyacetophenone in the solution was determined by the high-performance liquid chromatography.

TABLE 1

| | | | 98% retention temperature in thermogravimetric-differential thermal analysis (TG-DTA) | Amount of phenolic compound after hydrolysis resistance test | Example 1 | Example 2 | Example 3 | Example 4 |
|---|---|---|---|---|---|---|---|---|
| Resin composition (part(s) by mass) | Aromatic PC resin (A) | (A1) FN1500 Mv = 14,500 | | | 100 | — | 100 | 100 |
| | | (A2) FN1200 Mv = 11,500 | | | — | 100 | — | — |
| | Phosphorus-based compound (B) | (B1) Doverphos S-9228PC | 368° C. | 0.15 mass % | 0.05 | 0.05 | 0.05 | 0.05 |
| | | (B2) ADK STAB 2112 | 260° C. | 6 mass % | — | — | — | — |
| | | (B3) ADK STAB PEP-36 | 284° C. | 45 mass % | — | — | — | — |
| | Polyether compound (C) | (C1) POLYCERIN DC-1100 | | | 0.2 | — | — | — |
| | | (C2) POLYCERIN DC-1800E | | | — | 0.2 | 0.4 | — |
| | | (C3) UNIOX GT-201S | | | — | — | — | 0.2 |
| | | (C4) UNILUB 50DE-25 | | | — | — | — | — |
| | | (C5) EPIOL E-1000 | | | — | — | — | — |
| | | (C6) UNISAFE NKL-9520 | | | — | — | — | — |
| | | (C7) PEG-6000J | | | — | — | — | — |
| | Other additive | KR-511 | | | 0.05 | 0.05 | 0.05 | 0.05 |
| | | CELLOXIDE 2021P | | | 0.02 | 0.02 | 0.02 | 0.02 |
| YI value (50 mmW × 80 mmH × 5 mmT) | | | Molding at 280° C. | | 1.00 | 1.00 | 0.96 | 1.08 |
| | | | Molding at 360° C. | | 1.07 | 1.05 | 1.04 | 1.11 |
| o-Hydroxyacetophenone (ppm) | | | Molding at 280° C. | | 2.00 | 1.90 | 1.20 | 1.90 |
| | | | Molding at 360° C. | | 2.50 | 2.80 | 1.30 | 2.80 |
| YI value in 85° C. × 95% R temperature and humidity controlled test (40 mmW × 80 mmH × 3 mmT) | | | 0 hours | | 0.95 | 0.95 | 0.93 | 1.00 |
| | | | 500 hours | | 1.10 | 1.12 | 1.06 | 1.11 |

| | | | Example 5 | 6 | 8 | 9 | 10 | 11 | 12 |
|---|---|---|---|---|---|---|---|---|---|
| Resin composition (part(s) by mass) | Aromatic PC resin (A) | (A1) FN1500 Mv = 14,500 | 100 | 100 | 100 | 100 | 100 | 100 | — |
| | | (A2) FN1200 Mv = 11,500 | — | — | — | — | — | — | 100 |
| | Phosphorus-based compound (B) | (B1) Doverphos S-9228PC | 0.05 | 0.05 | 0.1 | 0.05 | 0.05 | 0.1 | 0.05 |
| | | (B2) ADK STAB 2112 | — | — | — | — | — | — | — |
| | | (B3) ADK STAB PEP-36 | — | — | — | — | — | — | — |
| | Polyether compound (C) | (C1) POLYCERIN DC-1100 | — | — | — | — | — | — | — |
| | | (C2) POLYCERIN DC-1800E | — | — | — | — | — | — | — |
| | | (C3) UNIOX GT-201S | — | — | — | — | — | — | — |
| | | (C4) UNILUB 50DE-25 | 0.2 | 0.4 | 0.4 | — | — | — | 0.6 |
| | | (C5) EPIOL E-1000 | — | — | — | 0.2 | — | — | — |
| | | (C6) UNISAFE NKL-9520 | — | — | — | — | 0.5 | — | — |
| | | (C7) PEG-6000J | — | — | — | — | — | 0.5 | — |
| | Other additive | KR-511 | 0.05 | 0.05 | 0.05 | 0.05 | 0.05 | 0.05 | 0.05 |
| | | CELLOXIDE 2021P | 0.02 | 0.02 | 0.02 | 0.02 | 0.02 | 0.02 | 0.02 |
| YI value (50 mmW × 80 mmH × 5 mmT) | | | 0.98 | 0.95 | 0.93 | 1.02 | 1.08 | 1.06 | 0.94 |
| | | | 1.03 | 0.96 | 0.93 | 1.08 | 1.11 | 1.11 | 0.98 |
| o-Hydroxyacetophenone (ppm) | | | 1.80 | 1.05 | 1.02 | 1.80 | 1.90 | 2.00 | 0.60 |
| | | | 2.60 | 1.06 | 1.04 | 2.50 | 2.80 | 2.70 | 0.80 |
| YI value in 85° C. × 95% R temperature and humidity controlled test (40 mmW × 80 mmH × 3 mmT) | | | 0.93 | 0.91 | 0.92 | 1.00 | 1.02 | 1.05 | 0.92 |
| | | | 1.00 | 1.04 | 1.12 | 1.15 | 1.13 | 1.18 | 1.06 |

TABLE 2

| | | | 98% retention temperature in thermogravimetric-differential thermal analysis (TG-DTA) | Amount of phenolic compound after hydrolysis resistance test | Comparative Example 1 | Comparative Example 2 |
|---|---|---|---|---|---|---|
| Resin composition (part(s) by mass) | Aromatic PC resin (A) | (A1) FN1500 Mv = 14,500 | | | 100 | 100 |
| | | (A2) FN1200 Mv = 11,500 | | | — | — |
| | Phosphorus-based compound (B) | (B1) Doverphos S-9228PC | 368° C. | 0.15 mass % | — | 0.05 |
| | | (B2) ADK STAB 2112 | 260° C. | 6 mass % | — | — |
| | | (B3) ADK STAB PEP-36 | 284° C. | 45 mass % | 0.05 | — |
| | Polyether compound (C) | (C1) POLYCERIN DC-1100 | | | — | — |
| | | (C4) UNILUB 50DE-25 | | | — | — |
| | Other additive | KR-511 | | | 0.05 | 0.05 |
| | | CELLOXIDE 2021P | | | 0.02 | 0.02 |
| YI value (50 mmW × 80 mmH × 5 mmT) | | | Molding at 280° C. | | 0.98 | 1.03 |
| | | | Molding at 360° C. | | 1.27 | 1.14 |
| o-Hydroxyacetophenone (ppm) | | | Molding at 280° C. | | 0.90 | 2.00 |
| | | | Molding at 360° C. | | 4.00 | 4.40 |

TABLE 2-continued

| | | | 0 hours | 0.95 | 0.99 |
|---|---|---|---|---|---|
| YI value in 85° C. × 95% R temperature and humidity controlled test (40 mmW × 80 mmH × 3 mmT) | | | 500 hours | 1.25 | 1.12 |

| | | | Comparative Example | | | | | |
|---|---|---|---|---|---|---|---|---|
| | | | 3 | 4 | 5 | 6 | 7 | 8 |
| Resin composition (part(s) by mass) | Aromatic PC resin (A) | (A1) FN1500 Mv = 14,500 | 100 | 100 | 100 | 100 | 100 | — |
| | | (A2) FN1200 Mv = 11,500 | — | — | — | — | — | 100 |
| | Phosphorus-based compound (B) | (B1) Doverphos S-9228PC | — | — | — | — | — | — |
| | | (B2) ADK STAB 2112 | — | 0.05 | — | — | — | — |
| | | (B3) ADK STAB PEP-36 | 0.05 | — | 0.05 | 0.05 | 0.1 | 0.05 |
| | Polyether compound (C) | (C1) POLYCERIN DC-1100 | 0.4 | 0.2 | — | — | — | — |
| | | (C4) UNILUB 50DE-25 | — | — | 0.2 | 0.4 | 0.4 | 0.4 |
| | Other additive | KR-511 | 0.05 | 0.05 | 0.05 | 0.05 | 0.05 | 0.05 |
| | | CELLOXIDE 2021P | 0.02 | 0.02 | 0.02 | 0.02 | 0.02 | 0.02 |
| YI value | | | 0.94 | 1.23 | 1.02 | 0.94 | 0.95 | 0.96 |
| (50 mmW × 80 mmH × 5 mmT) | | | 1.08 | 1.35 | 1.15 | 1.03 | 0.96 | 1.00 |
| o-Hydroxyacetophenone (ppm) | | | 0.70 | 2.50 | 1.00 | 0.70 | 0.70 | 0.70 |
| | | | 1.90 | 5.00 | 2.50 | 1.80 | 1.70 | 1.80 |
| YI value in 85° C. × 95% R temperature and humidity controlled test (40 mmW × 80 mmH × 3 mmT) | | | 0.93 | 1.20 | 0.93 | 0.91 | 0.91 | 0.91 |
| | | | 1.45 | 2.00 | 1.30 | 1.35 | 3.13 | 1.50 |

In Comparative Example 1 free of any polyether, the color tone is satisfactory in the low-temperature molding, but the color tone is poor in the high-temperature molding, and the difference between the color tones in the low-temperature molding and the high-temperature molding is large. In Comparative Example 2 similarly free of any polyether and containing the specific phosphorus-based compound (B), the color tone in the high-temperature molding is acceptable, but the color tone in the low-temperature molding is insufficient. In each of Comparative Examples 3 and 6 containing a polyether, the color tones in the low-temperature molding and the high-temperature molding are somewhat satisfactory, but the reduction in color tone after the hydrolysis resistance test is large. In Comparative Example 3, not only yellowing but also opacification of the molded body occurred. In Comparative Example 4 in which such phosphorus-based compound that the amount of a compound having a phenol structure to be produced after the hydrolysis resistance test is more than 5 mass % is used, the reduction in color tone in association with the hydrolysis of the molded body is remarkable. It is because there is a high possibility that the hydrolysis occurred that the color tone is poor in Comparative Example 4 despite the presence of the polyether. In each of Comparative Examples 5 and 6, the color tones after the molding at the low and high temperatures fall within the standards, but the difference ΔYI between the YI values before and after the moist heat resistance test is large. In Comparative Example 7, the hydrolysis resistance remarkably reduced as a result of the increase in amount of the phosphorus-based compound to 0.1 part by mass. In Comparative Example 8, the molded body becomes liable to hydrolyze owing to the reduction in molecular weight of the polycarbonate resin.

In contrast, it is found that in each of Examples 1 to 9 in which the phosphorus-based compound (B) having the following features and the polyether compound (C) are used in combination, the yellowing of the composition is suppressed irrespective of which one of the temperatures, i.e., 280° C. and 360° C. the composition is molded at, and hence the molding can be performed in a wide temperature region without the yellowing: a decomposition temperature is high and the amount of a compound having a phenol structure to be produced after the hydrolysis resistance test is 5 mass % or less. High hydrolysis resistance was observed also in the moist heat resistance test.

INDUSTRIAL APPLICABILITY

The polycarbonate resin composition of the present invention is suitable for an optical product, such as a light-guiding plate, specifically a large-screen and thin display commodity, such as a smart phone or a tablet PC, because the composition is excellent in heat stability in high-temperature molding and can provide a molded article that is not reduced in optical characteristics by its deterioration at the time of its molding even when molded in a wide temperature region. Meanwhile, the composition is also useful as an optical material for low-temperature molding.

The invention claimed is:

1. A polycarbonate resin composition, comprising, with respect to 100 parts by mass of an aromatic polycarbonate resin (A), 0.005 part by mass to 1 part by mass of a phosphorus-based compound (B) having an aryl group, and 0.005 part by mass to 5 parts by mass of a polyether compound (C) having a polyoxyalkylene structure, wherein:

an amount of a compound having a phenol structure produced by decomposition of the phosphorus-based compound (B) 1,500 hours after standing thereof under conditions of 40° C. and a humidity of 90% is 5 mass % or less with respect to the phosphorus-based compound (B);

when a weight of the phosphorus-based compound (B) is measured with a thermogravimetric-differential thermal analysis (TG-DTA) machine under a nitrogen atmosphere, a temperature at which the weight becomes smaller than the weight before the measurement by 2% is 340° C. or more; and the polyether compound (C) is represented by the following formula (1):

$$R^{C3}O-(R^{C1}O)_m(R^{C2}O)_n-R^{C4} \quad (1)$$

wherein $R^{C1}$ and $R^{C2}$ each represent a methylene group, an ethylene group, a trimethylene group, a propylene group, or a hexamethylene group, and $R^{C3}$ and $R^{C4}$ each represent a hydrogen atom, a hydrocarbon group having 1 to 30 carbon atoms, an alkanoyl group having 1 to 30 carbon atoms, an alkenoyl group having 2 to 30 carbon atoms, or a glycidyl group, and $R^{C3}$ and $R^{C4}$ may be identical to or different from each other.

2. The polycarbonate resin composition according to claim 1, wherein the aromatic polycarbonate resin (A) comprises a polycarbonate comprising, in a main chain thereof, a repeating unit represented by the following general formula (I):

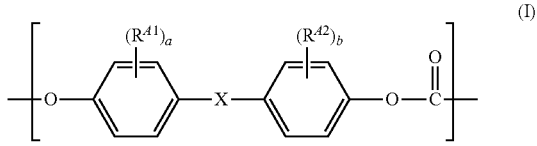

(I)

wherein $R^{A1}$ and $R^{A2}$ each represent an alkyl group or alkoxy group having 1 to 6 carbon atoms, and $R^{A1}$ and $R^{A2}$ may be identical to or different from each other, X represents a single bond, an alkylene group having 1 to 8 carbon atoms, an alkylidene group having 2 to 8 carbon atoms, a cycloalkylene group having 5 to 15 carbon atoms, a cycloalkylidene group having 5 to 15 carbon atoms, —S—, —SO—, —SO$_2$—, —O—, or —CO—, and a and b each independently represent an integer of from 0 to 4, when a represents 2 or more, $R^{A1}$'s may be identical to or different from each other, and when b represents 2 or more, $R^{A2}$'s may be identical to or different from each other.

3. The polycarbonate resin composition according to claim 1, wherein the phosphorus-based compound (B) having an aryl group comprises a phosphorus-based compound having a phosphite structure.

4. The polycarbonate resin composition according to claim 1, wherein the phosphorus-based compound (B) having an aryl group comprises a pentaerythritol diphosphite compound represented by the following general formula (II):

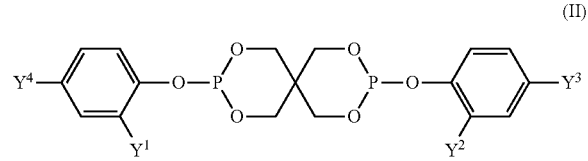

(II)

wherein $Y^1$ to $Y^4$ each represent a hydrocarbon group having 6 to 15 carbon atoms, and may be identical to or different from each other.

5. The polycarbonate resin composition according to claim 4, wherein $Y^1$ to $Y^4$ in the formula (II) each represent a cumyl group that may be unsubstituted or substituted, a phenyl group that may be unsubstituted or substituted, a naphthyl group that may be unsubstituted or substituted, or a biphenyl group that may be unsubstituted or substituted.

6. The polycarbonate resin composition according to claim 1, wherein the phosphorus-based compound (B) having an aryl group comprises a pentaerythritol diphosphite compound represented by the following general formula (II-1):

wherein $R^{B1}$ to $R^{B8}$ each represent an alkyl group or an alkenyl group, and may be identical to or different from each other, and $R^{B1}$ and $R^{B2}$, $R^{B3}$ and $R^{B4}$, $R^{B5}$ and $R^{B6}$, or $R^{B7}$ and $R^{B8}$ may be bonded to each other to form a ring, $R^{B9}$ to $R^{B12}$ each represent a hydrogen atom or an alkyl group, and may be identical to or different from each other, m1 to m4 each represent an integer of from 0 to 5, and may be identical to or different from each other, and $Z^1$ to $Z^4$ each represent a single bond or a carbon atom, and may be identical to or different from each other, and when $Z^1$ to $Z^4$ each represent a single bond, $R^{B1}$ to $R^{B8}$ are excluded from the general formula (II-1).

7. The polycarbonate resin composition according to claim 1, wherein the phosphorus-based compound (B) having an aryl group comprises bis(2,4-dicumylphenyl)pentaerythritol diphosphite.

8. The polycarbonate resin composition according to claim 1, wherein the polyether compound (C) comprises a polyoxyalkylene glycol in which in the formula (1), $R^{C1}$ and $R^{C2}$ each represent an ethylene group, or a propylene group, and $R^{C3}$ and $R^{C4}$ each represent a hydrogen atom.

9. The polycarbonate resin composition according to claim 1, wherein the aromatic polycarbonate resin (A) has a viscosity-average molecular weight (Mv) of from 9,000 to 50,000.

10. The polycarbonate resin composition according to claim 1, wherein an amount of o-hydroxyacetophenone measured by the following measurement method (2) is 2.0 ppm by mass or less, and an amount of o-hydroxyacetophenone measured by the following measurement method (1) is twice or less as large as the amount of o-hydroxyacetophenone measured by the measurement method (2):

measurement method (1)

the polycarbonate resin composition is pelletized, followed by drying, and is then molded into a molded body measuring 50 mm by 80 mm by 5 mm thick by an injection molding method at a cylinder temperature of 360° C. and a die temperature of 80° C. for a cycle time of 50 seconds, the molded body is pulverized and dissolved in chloroform, and an amount of o-hydroxyacetophenone in the solution is determined by high-performance liquid chromatography; and measurement method (2)

the polycarbonate resin composition is pelletized, followed by drying, and is then molded into a molded body measuring 50 mm by 80 mm by 5 mm thick by the injection molding method at a cylinder temperature of 280° C. and a die temperature of 80° C. for a cycle time of 50 seconds, the molded body is pulverized and dissolved in chloroform, and an

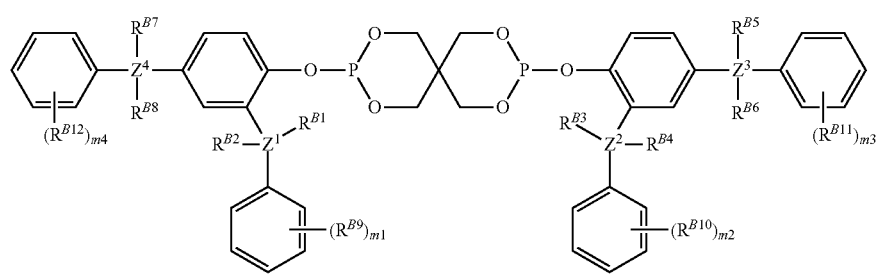

(II-1)

amount of o-hydroxyacetophenone in the solution is determined by the high-performance liquid chromatography.

11. The polycarbonate resin composition according to claim 1, wherein YI values measured by the following measurement methods (3) and (4) are 1.2 or less, and a difference between the YI values measured by the measurement method (3) and the measurement method (4) is 0.1 or less:

measurement method (3)
the polycarbonate resin composition is pelletized, followed by drying, and is then molded into a molded body measuring 50 mm by 80 mm by 5 mm thick by an injection molding method at a cylinder temperature of 360° C. and a die temperature of 80° C. for a cycle time of 50 seconds, and a YI value of the molded body is measured with a spectrophotometer under conditions of a C light source and a two-degree field of view; and measurement method (4)
the polycarbonate resin composition is pelletized, followed by drying, and is then molded into a molded body measuring 50 mm by 80 mm by 5 mm thick by the injection molding method at a cylinder temperature of 280° C. and a die temperature of 80° C. for a cycle time of 50 seconds, and a YI value of the molded body is measured with the spectrophotometer under conditions of a C light source and a two-degree field of view.

12. A method of producing an optical molded article, comprising molding the polycarbonate resin composition of claim 1 at a temperature of from 280° C. to 360° C.

13. An optical molded article, which is obtained by the production method of claim 12.

14. The optical molded article according to claim 13, wherein the optical molded article comprises a light-guiding member.

15. The polycarbonate resin composition according to claim 1, wherein the polyether compound (C) comprises a polyoxyalkylene glycol in which in the formula (1), $R^{C1}$ represents an ethylene group and $R^{C2}$ represents a propylene group, and $R^{C3}$ and $R^{C4}$ each represent a hydrogen atom.

* * * * *